United States Patent [19]

van den Bosch et al.

[11] 4,332,829
[45] Jun. 1, 1982

[54] METHYLTHIOMETHYL ESTERS AS FLAVOR ADDITIVES

[75] Inventors: Steven van den Bosch, Woudenberg; Evert van't Land, Terschuur; Jan Stoffelsma, Hoevelaken, all of Netherlands

[73] Assignee: Polak's Frutal Works, B.V., Amersfoort, Netherlands

[21] Appl. No.: 231,184

[22] Filed: Feb. 2, 1981

Related U.S. Application Data

[63] Continuation-in-part of Ser. No. 52,154, Jun. 26, 1979, abandoned.

[30] Foreign Application Priority Data

Jul. 18, 1978 [GB] United Kingdom ............... 30161/78

[51] Int. Cl.$^3$ ...................... A23L 1/226; A23L 1/235
[52] U.S. Cl. .................................... 426/535; 560/222; 560/231; 260/399

[58] Field of Search .......................................... 426/535

[56] References Cited

U.S. PATENT DOCUMENTS

| | | | |
|---|---|---|---|
| 3,870,800 | 3/1975 | Pettet et al. | 426/535 |
| 3,900,581 | 8/1975 | Wenter et al. | 426/535 |
| 3,978,240 | 8/1976 | van der Heijden et al. | 426/535 |

OTHER PUBLICATIONS

Fenaroli's Handbook of Flavor Ingredients, 2nd Ed., 1975, Edited by Furia et al., CRC Press: Cleveland, pp. 132, 133, 185, 202, 207, 208.

*Primary Examiner*—Joseph M. Golian
*Attorney, Agent, or Firm*—William S. Alexander

[57] ABSTRACT

Methylthiomethyl esters of aliphatic acids have been found useful in imparting or enhancing flavors in foodstuffs. They are particularly useful with respect to fruit and berry flavors.

33 Claims, No Drawings

METHYLTHIOMETHYL ESTERS AS FLAVOR ADDITIVES

This application is a continuation-in-part of our copending application Ser. No. 52,154, filed June 26, 1979, and now abandoned.

This invention relates to the use of methylthiomethyl esters of aliphatic acids as flavor additives and to flavoring compositions and foodstuffs containing such compounds.

Food scientists and researches are constantly striving to improve or strengthen the flavor and the flavor impact of foodstuffs by use of flavor additives to replace flavor lost by the processing or in storage or to impart a "natural" flavor effect to a reconstituted foodstuff. Considerable effort is also being put into developing flavor compounds and flavoring compositions for imparting flavors to otherwise bland or tasteless, though nutritionally useful, materials.

In accordance with this invention, there are provided flavoring compositions or flavor enhancing compositions containing methylthiomethyl esters of aliphatic acids, represented by the structural formula R—COOCH$_2$SCH$_3$ wherein R is selected from the group consisting of hydrogen, alkyl radicals with 1 to 9 carbon atoms, alkenyl radicals with 2 to 9 carbon atoms and polyunsaturated alkyl radicals with 4 to 9 carbon atoms. When R represents one of the above described alkyl groups, the alkyl group can be straight-chain or branched-chain. Some of the compounds presented in this invention exist in isomeric forms, and the compounds given herein include such isomers and mixtures thereof.

Although some of the compounds used in the present invention are known in literature, there is no disclosure in the prior art indicating that they possess flavoring properties. The following methylthiomethyl esters of the aliphatic series are known from the chemical literature: the acetate, the propionate, the octanoate, the acrylate, and the methacrylate (see e.g., Chem. Abstr., 83, 192168U, Tetrah. Letters, 1972, 4941–4, J. Amer. Chem. Soc., 92, 6521–5 (1970), Tetrahedron, 19, 817–20 (1963), Can. J. Chem. 42, 2357–62 (1964), Chem. Abstr., 59, 3806g, Ann., 626, 19–25 (1959), Syn. Comm., 3, 145–6 (1973), J.C.S. Chem. Comm., 1973, 224–5, Chem. Abstr., 72, 54677f, and J. Amer. Chem. Soc., 91, 682–7 (1969)).

As stated, the methylthiomethyl esters of this invention exhibit a wide variety of flavor effects giving rise to a wide field of uses. In particular, they are useful in fruit flavors, e.g., pineapple, strawberry, raspberry, blackcurrant, mango, durian, grape, apple, peach, pear, and other fruit and berry flavors. The esters are also useful in cheese, cream, milk, meat, and vegetable flavors.

The following table illustrates some of the great variety of flavor effects exhibited by the compounds presented in the invention.

| Methylthiomethyl ester of | Organoleptic property |
| --- | --- |
| formic acid | cabbage, meaty, onion, metallic |
| acetic acid | estery, milky, cabbage, meat, sulfury |
| propionic acid | dairy-like, yoghurt, sulfury |
| butyric acid | cabbage, milky, cheese |
| isobutyric acid | strawberry, pineapple |
| 2-methylbutyric acid | fruity, strawberry, pineapple, mango, durian |
| valeric acid | fruity, cheese, milky |
| isovaleric acid | blackcurrant, tropical fruits |
| hexanoic acid | pineapple, fruity |
| heptanoic acid | fruity, pineapple, pear |
| octanoic acid | dairy-like, fruity, cheese |
| tiglic acid | sweet apple, fruity |
| 2-hexenoic acid | green, cream, earthy, fatty |
| 2-methyl-2-pentenoic acid | fruity, pear, sulfury |
| geranic acid | aldehydic, fruity, estery |
| citronellic acid | aldehydic, wine, earthy |
| lavandulic acid | grape, radish, cabbage |

The methylthiomethyl esters of this invention can be employed singly or in admixture of two or more. They all can be employed as components either of flavoring compositions or of flavor-enhancing compositions.

A flavoring composition means a combination of ingredients compounded to supply or impart a specific flavor character to an otherwise bland ingestible material, or to completely change an existing flavor. A flavor-enhancing composition is a combination of ingredients which, in combination, are capable of reinforcing one or more flavor notes of a natural or other foodstuff to improve, supplement or augment a flavor which has been undesirably diminished or otherwise altered by processing or which is inferior due to the general quality of the foodstuff initially. Either type of composition is usually suspended or dissolved in an organoleptically inert carrier, although this is not absolutely necessary.

When used in fruit or berry flavoring compositions, additional flavoring compounds typically used in combination with the methylthiomethyl esters of the invention include, e.g.

| | |
| --- | --- |
| orange oil | isoamyl acetate |
| phenyl ethyl isovalerate | fusel oil |
| damascenone | lie de vin |
| ethyl maltol | 2-methyl butanol |
| 2-methylbutyric acid | phenylethyl alcohol |
| angelica root oil | trans-2-hexenol |
| buchu oil | methyl anthranilate |
| cognac oil | 2-methyl-2-pentenoic acid |
| petitgrain oil | vanillin |
| cedar leaf oil | maltol |
| isoamyl isovalerate | benzyl alcohol |
| methyl butyrate | linaolool |
| isobutyl acetate | isoamyl butyrate |
| methyl isobutyl carbinyl acetate | ethyl acetate |
| | ethyl butyrate |
| ethyl benzoate | ethyl hexanoate |
| citral | ethyl heptanoate |
| cuminic aldehyde | cis-3-hexenol |
| beta-ionone | ethyl isovalerate |
| tangerine oil | phenyl butyrate |
| benzyl acetate | amyl acetate |
| orange peel oil | geranyl acetate |
| bergamot oil | gamma-nonalactone |
| lime oil | Ylang Ylang |
| orange terpenes | beta-terpineol |
| methyl cinnamate | |

When used in dairy type flavors-i.e., cheese, butter, or cream flavors, additional flavoring compositions typically used in combination with the methylthiomethyl esters of the invention include:

| | |
| --- | --- |
| delta-decalactone | 2-heptanone |
| heliotropin | gamma-undecalactone |
| butyric acid | ethyl lactate |
| hexanoic acid | gamma-decalactone |

| | |
|---|---|
| isovaleric acid | acetoin |
| octanoic acid | diacetyl |

The term "foodstuff" includes both solid and liquid ingestible materials which usually do, but need not, have nutritional value. Thus, foodstuffs include fruit juices, fruit flavored beverages, puddings, jellies, pastries, ice cream, candies, chewing gum, dairy products, vegetables, cereals, meats, soups, convenience foods and the like. They can also be employed to restore the fresh fruit effect of canned and frozen fruits.

The amount of methylthiomethyl ester added to a foodstuff needs to be only the amount sufficient to impart or to enhance the desired flavor. Small amounts are effective, though the amount can be varied over a wide range depending upon the flavor strength required. Generally, the amount will be between about 0.1 to 5 parts per million by weight based on the foodstuff being flavored.

To prepare the methylthiomethyl esters described in this invention, the corresponding acid is reacted with chloromethyl methyl sulfide in the presence of one equivalent of an amine, for example, triethylamine (T. L. Ho and C. M. Wong, J. Chem. Soc. Chem. Comm., 1973, 224–225).

The following examples are intended to illustrate the invention, but not to limit the same in any way.

EXPERIMENTAL PART

NMR spectra were recorded on a JEOL FX-100 instrument as solutions in $CDCl_3$ with tetramethylsilane as internal standard.

IR spectra were measured with a Perkin-Elmer 225 Spectrophotometer, neat or as solutions in $CCl_4$.

EXAMPLE 1

Preparation of Methylthiomethyl Hexanoate

In a three-necked 1000 ml. round-bottomed flask fitted with a mechanical stirrer, thermometer and reflux condenser is placed 63.8 g. of hexanoic acid in 200 ml. of acetonitrile. To the stirred mixture is added, at 20°–30° C., 55 g. of triethylamine over a period of 30 minutes. The reaction mixture is stirred at room temperature for an additional 60 minutes. Then is added, at 20°–24° C., 53 g. of chloromethyl methyl sulfide in a few minutes. The reaction mixture is warmed and allowed to reflux for 24 hours. The reaction mixture is cooled to 5°–0° C. and filtered. The solvent is stripped off under vacuum at 12 mm Hg pressure. The residue is taken up in diethyl ether and washed successively with a 10% solution of sodium bicarbonate and with water. The organic layer is dried over anhydrous sodium sulfate. Distillation gives the title ester; b.p. 57°–58° C./2 mm Hg, $n_D^{20}$ 1.4545.

Spectral data of the compound:

| NMR SPECTRUM ($\delta$ in ppm) | IR spectrum (neat) |
|---|---|
| $\delta = 0.88$ (t, 3H) | 2960, 2930, 2875, 2860, 1731(s), |
| $\delta = 1$–1.8 (-, 6H) | 1470, 1417, 1220, 1162(s), 1106, |
| $\delta = 2.23$ (s, 3H) | 1095, 964, 917, 750, 700 cm$^{-1}$. |
| $\delta = 2.33$ (t, 2H) | |
| $\delta = 5.12$ (s, 2H) | |

EXAMPLE 2

Preparation of Methylthiomethyl Formate

This product was prepared according to the procedure described in Example 1, by reacting formic acid with chloromethyl methyl sulfide in the presence of one equivalent of triethylamine; b.p. 35° C./12 mm Hg, $n_D^{20}$ 1.4650.

Spectral data of the compound:

| NMR spectrum ($\delta$ in ppm) | IR spectrum (neat) |
|---|---|
| $\delta = 2.26$ (s, 3H) | 2925, 1720, 1430, 1310, 1262, |
| $\delta = 5.22$ (s, 2H) | 1130, 1010, 909, 870, 750, 694 |
| $\delta = 8.11$ (t, 1H) | 429 cm$^{-1}$. |

EXAMPLE 3

Preparation of Methylthiomethyl Acetate

This product was prepared according to the procedure described in Example 1, by reacting acetic acid with chloromethyl methyl sulfide in the presence of one equivalent of triethylamine; b.p. 45°–46° C./12 mm Hg, $n_D^{20}$ 1.4570.

Spectral data of the compound:

| NMR spectrum ($\delta$ in ppm) | IR spectrum (neat) |
|---|---|
| $\delta = 2.07$ (s, 3H) | 2925, 1740(s), 1426, 1369, 1310, |
| $\delta = 2.12$ (s, 3H) | 1210(s), 1018, 1008, 960, 910, |
| $\delta = 5.10$ (s, 2H) | 812, 749, 697, 600, 462 cm$^{-1}$. |

EXAMPLE 4

Preparation of Methylthiomethyl Propionate

This product was prepared according to the procedure described in Example 1, by reacting propionic acid with chloromethyl methyl sulfide in the presence of one equivalent of triethylamine; b.p. 58°–59° C./12 mm Hg, $n_D^{20}$ 1.4548.

Spectral data of the compound:

| NMR spectrum ($\delta$ in ppm) | IR spectrum (neat) |
|---|---|
| $\delta = 1.15$ (t, 3H) | 2985, 2945, 2925, 1740, 1460, |
| $\delta = 2.24$ (s, 3H) | 1423, 1356, 1263, 1160, 1078, |
| $\delta = 2.36$ (q, 2H) | 995, 934, 805, 749, 696 cm$^{-1}$. |
| $\delta = 5.13$ (s, 2H) | |

EXAMPLE 5

Preparation of Methylthiomethyl Butyrate

This product was prepared according to the procedure described in Example 1, by reacting butyric acid with chloromethyl methyl sulfide in the presence of one equivalent of triethylamine; b.p. 71°–73° C./12 mm Hg, $n_D^{20}$ 1.4521.

Spectral data of the compound:

| NMR spectrum ($\delta$ in ppm) | IR spectrum (neat) |
|---|---|
| $\delta = 0.96$ (t, 3H) | 2970, 2940, 2880, 1740(s), 1460, |
| $\delta = 1.66$ (m, 2H) | 1418, 1363, 1312, 1260, 1240, |
| $\delta = 2.23$ (s, 3H) | 1156(s), 1098, 1080, 1035, |
| $\delta = 2.33$ (t, 2H) | 964(s), 920, 750, 696 cm$^{-1}$. |
| $\delta = 5.13$ (s, 2H) | |

EXAMPLE 6

Preparation of Methylthiomethyl Isobutyrate

This product was prepared according to the procedure described in Example 1, by reacting isobutyric acid with chloromethyl methyl sulfide in the presence of one equivalent of triethylamine; b.p. 64° C./12 mm Hg, $n_D^{20}$ 1.4470.

Spectral data of the compound:

| NMR spectrum (δ in ppm) | IR spectrum (neat) |
| --- | --- |
| δ = 1.19 (d, 6H) | 2975, 2920, 2875, 1735(s), 1468, |
| δ = 2.22 (s, 3H) | 1424, 1385, 1358, 1234, 1181, |
| δ = 2.56 (m, 1H) | 1134(s), 1053, 1015, 957, 916, |
| δ = 5.12 (s, 2H) | 880, 800, 760, 696 cm$^{-1}$. |

EXAMPLE 7

Preparation of Methylthiomethyl Valerate

This product was prepared according to the procedure described in Example 1, by reacting valeric acid with chloromethyl methyl sulfide in the presence of one equivalent of triethylamine; b.p. 83°–85° C./12 mm Hg, $n_D^{20}$ 1.4560.

Spectral data of the compound:

| NMR spectrum (δ in ppm) | IR spectrum (neat) |
| --- | --- |
| δ = 0.92 (t, 3H) | 2960, 2930, 2880, 1739(s), 1465, |
| δ = 1–1.8 (m, 4H) | 1416, 1260, 1225, 1150(s), 1103, |
| δ = 2.22 (s, 3H) | 1083, 960, 948, 746, 695 cm$^{-1}$. |
| δ = 2.32 (t, 2H) | |
| δ = 5.12 (s, 2H) | |

EXAMPLE 8

Preparation of Methylthiomethyl Isovalerate

This product was prepared according to the procedure described in Example 1, by reacting isovaleric acid with chloromethyl methyl sulfide in the presence of one equivalent of triethylamine; b.p. 78°–79° C./12 mm Hg, $n_D^{20}$ 1.4496.

Spectral data of the compound:

| NMR spectrum (δ in ppm) | IR spectrum (neat) |
| --- | --- |
| δ = 0.92 (d, 6H) | 2960, 2920, 2875, 1736(s), 1467, |
| δ = 1.6 (m, 3H) | 1425, 1366, 1310, 1284, 1237, |
| δ = 2.21 (s, 3H) | 1174, 1156(s), 1105, 1085, 975(s), |
| δ = 5.12 (s, 2H) | 940, 747, 693 cm$^{-1}$. |

EXAMPLE 9

Preparation of Methylthiomethyl 2-Methylbutyrate

This product was prepared according to the procedure described in Example 1, by reacting 2-methylbutyric acid with chloromethyl methyl sulfide in the presence of one equivalent of triethylamine; b.p. 75°–77° C./12 mm Hg, $n_D^{20}$ 1.4505.

Spectral data of the compound:

| NMR spectrum (δ in ppm) | IR spectrum (neat) |
| --- | --- |
| δ = 0.92 (t, 3H) | 2985, 2930, 2875, 1736(s), 1460, |
| δ = 1.16 (d, 3H) | 1424, 1380, 1360, 1309, 1258, |
| δ = 1.56 (m, 2H) | 1220, 1170, 1133(s), 1064, 1000, |
| δ = 2.23 (s, 3H) | 966, 940, 756, 693 cm$^{-1}$. |
| δ = 2.40 (m, 1H) | |

-continued

| NMR spectrum (δ in ppm) | IR spectrum (neat) |
| --- | --- |
| δ = 5.13 (s, 3H) | |

EXAMPLE 10

Preparation of Methylthiomethyl Tiglate

This product was prepared according to the procedure described in Example 1, by reacting tiglic acid with chloromethyl methyl sulfide in the presence of one equivalent of triethylamine; b.p. 95° C./12 mm Hg, $n_D^{20}$ 1.4890.

Spectral data of the compound:

| NMR spectrum (δ in ppm) | | IR spectrum (neat) |
| --- | --- | --- |
| δ = 0.80 | d, | 2980, 2920, 1710(s), 1647, 1430, |
| δ = 0.84 | 6H s, | 1377, 1340, 1310, 1248(s), 1240(s) |
| δ = 2.24 | (s, 3H) | 1140, 1116(s), 1080, 1060, 1014, |
| δ = 5.20 | (s, 2H) | 961, 920, 745, 725 cm$^{-1}$. |
| δ = 6.80 | (q, 1H) | |

EXAMPLE 11

Preparation of Methylthiomethyl 2-Hexenoate

This product was prepared according to the procedure described in Example 1, by reacting 2-hexenoic acid with chloromethyl methyl sulfide in the presence of one equivalent of triethylamine; b.p. 75°–76° C./2 mm Hg, $n_D^{20}$ 1.4836.

Spectral data of the compound:

| NMR spectrum (δ in ppm) | IR spectrum (neat) |
| --- | --- |
| δ = 0.94 (t, 3H) | 2960, 2930, 2875, 1723, 1650, |
| δ = 1.48 (m, 2H) | 1424, 1333, 1313, 1237, 1158, |
| δ = 2.2 (m, 2H) | 1117, 1041, 984, 925, 750, |
| δ = 2.24 (s, 3H) | 695 cm$^{-1}$. |
| δ = 5.19 (s, 2H) | |
| δ = 5.84 (d, 1H) | |
| δ = 7.0 (m, 1H) | |

EXAMPLE 12

Preparation of Methylthiomethyl 2-Methyl-2-pentenoate

This product was prepared according to the procedure described in Example 1, by reacting 2-methyl-2-pentenoic acid with chloromethyl methyl sulfide in the presence of one equivalent of triethylamine; b.p. 56°–57° C./2 mm Hg, $n_D^{20}$ 1.4861.

Spectral data of the compound:

| NMR spectrum (δ in ppm) | IR spectrum (neat) |
| --- | --- |
| δ = 1.05 (t, 3H) | 2965, 2930, 2875, 1720, 1649, |
| δ = 1.84 (s, 3H) | 1439, 1334, 1314, 1263, 1233, |
| δ = 2.2 (m, 2H) | 1154, 1132, 1095, 1076, 990, |
| δ = 2.24 (s, 3H) | 940, 750 cm$^{-1}$. |
| δ = 5.20 (s, 2H) | |
| δ = 6.81 (t, 1H) | |

EXAMPLE 13

Preparation of Methylthiomethyl Heptanoate

This product was prepared according to the procedure described in Example 1, by reacting heptanoic acid with chloromethyl methyl sulfide in the presence of one equivalent of triethylamine; b.p. 80°–81° C./2 mm Hg, $n_D^{20}$ 1.4591.

Spectral data of the compound:

| NMR spectrum ($\delta$ in ppm) | IR spectrum (neat) |
|---|---|
| $\delta$ = 0.89 (t, 3H) | 2960, 2925, 2860, 1740(s), 1466, |
| $\delta$ = 1–1.8 (-, 8H) | 1455, 1415, 1360, 1330, 1310, |
| $\delta$ = 2.23 (s, 3H) | 1260, 1220, 1145(s), 1100, 973, |
| $\delta$ = 2.35 (t, 2H) | 956, 746, 723, 695 cm$^{-1}$. |
| $\delta$ = 5.12 (s, 2H) | |

EXAMPLE 14

Preparation of Methylthiomethyl Octanoate

This product was prepared according to the procedure described in Example 1, by reacting octanoic acid with chloromethyl methyl sulfide in the presence of one equivalent of triethylamine; b.p. 90° C./2 mm Hg, $n_D^{20}$ 1.4577.

Spectral data of the compound:

| NMR spectrum ($\delta$ in ppm) | IR spectrum (neat) |
|---|---|
| $\delta$ = 0.88 (t, 3H) | 2955, 2920, 2860, 1734(s), 1460, |
| $\delta$ = 1–1.8 (-, 10H) | 1409, 1370, 1327, 1305, 1254, |
| $\delta$ = 2.23 (s, 3H) | 1210, 1140(s), 1100, 960, 742, |
| $\delta$ = 2.34 (t, 2H) | 716, 692 cm$^{-1}$. |
| $\delta$ = 5.12 (s, 2H) | |

EXAMPLE 15

Preparation of Methylthiomethyl Citronellate

This product was prepared according to the procedure described in Example 1, by reacting citronellic acid with chloromethyl methyl sulfide in the presence of one equivalent of triethylamine; b.p. 110° C./2 mm Hg, $n_D^{20}$ 1,4760.

Spectral data of the compound:

| NMR spectrum ($\delta$ in ppm) | IR spectrum (neat) |
|---|---|
| $\delta$ = 0.96 (d, 3H) | 2960, 2920, 2855, 1740(s), 1434, |
| $\delta$ = 1.58 (s, 3H) | 1374, 1330, 1310, 1280, 1216, |
| $\delta$ = 1.67 (s, 3H) | 1170, 1130, 1072, 970, 746, |
| $\delta$ = 2.12 (s, 3H) | 692 cm$^{-1}$. |
| $\delta$ = 5.10 (s, 2H) | |

EXAMPLE 16

Preparation of Methylthiomethyl Geranate

This product was prepared according to the procedure described in Example 1, by reacting geranic acid with chloromethyl methyl sulfide in the presence of one equivalent of triethylamine; b.p. 111°–112° C./2 mm Hg, $n^{20}$ 1.4912.

Spectral data of the compound:

| NMR spectrum ($\delta$ in ppm) | IR spectrum (neat) |
|---|---|
| $\delta$ = 1.62 (s, 3H) | 2965, 2920, 2855, 1720(s), 1641, |
| $\delta$ = 1.70 (s, 3H) | 1435, 1373, 1356, 1210, 1125(s), |
| $\delta$ = 2.18 (-, 7H) | 1050, 974, 929, 860, 815, 748, |
| $\delta$ = 2.24 (s, 3H) | 693 cm$^{-1}$. |
| $\delta$ = 5.08 (-, 1H) | |
| $\delta$ = 5.16 (s, 2H) | |
| $\delta$ = 5.70 (s, 1H) | |

EXAMPLE 17

Preparation of Methylthiomethyl Lavandulate

This product was prepared according to the procedure described in Example 1, by reacting lavandulic acid with chloromethyl methyl sulfide in the presence of one equivalent of triethylamine; b.p. 93°–94° C./2 mm Hg, $n^{20}$ 1.4855.

Spectral data of the compound:

| NMR spectrum ($\delta$ in ppm) | Ir spectrum (neat) |
|---|---|
| $\delta$ = 1.63  s | 3080, 2970, 2925, 1738(s), 1644, |
| $\delta$ = 1.67  (s, 9H) | 1435, 1384, 1340, 1255, 1166, |
| $\delta$ = 1.78  s | 1130(s), 984, 965, 925, 895, |
| $\delta$ = 2.20  (s, 3H) | 770, 744, 694 cm$^{-1}$. |
| $\delta$ = 3.06  (t, 3H) | |
| $\delta$ = 5.12  (s, 2H) | |

EXAMPLE 18

Two cheese flavor enhancing compositions were prepared by mixing the following ingredients:

| | A | B |
|---|---|---|
| butyric acid | 30 | 30 |
| hexanoic acid | 3 | 3 |
| isovaleric acid | 3 | 3 |
| octanoic acid | 5 | 5 |
| 2-heptanone | 2 | 2 |
| $\gamma$-undecalactone | 0.5 | 0.5 |
| ethyl lactate | 10 | 10 |
| $\gamma$-decalactone | 0.5 | 0.5 |
| $\gamma$-dodecalactone | 0.5 | 0.5 |
| acetoin | 0.2 | 0.2 |
| diacetyl | 0.1 | 0.1 |
| methylcinnamate | 0.5 | 0.5 |
| methylthiomethyl hexanoate | — | 0.5 |
| propylene glycol | 944.7 | 944.2 |
| | 1000.0 | 1000.0 |

Mixtures A and B were added separately to a commercially available low caloric processed cheese (20% fat content) at a level of 4 g. per kilogram. The processed cheese containing mixture A was compared with the processed cheese containing mixture B. The processed cheese containing mixture B was preferred over the processed cheese containing mixture A, because it had a more pronounced cheese taste with an increased creamy character.

EXAMPLE 19

Three pineapple flavor compositions were prepared by mixing the following ingredients:

| | A | B | C |
|---|---|---|---|
| vanillin | 16 | 16 | 16 |
| maltol | 16 | 16 | 16 |
| benzylalcohol | 80 | 80 | 80 |
| linalool | 8 | 8 | 8 |
| isoamyl butyrate | 24 | 24 | 24 |

-continued

|  | A | B | C |
|---|---|---|---|
| ethyl acetate | 32 | 32 | 32 |
| ethyl butyrate | 32 | 32 | 32 |
| ethyl hexanoate | 64 | 64 | 64 |
| ethyl heptanoate | 48 | 48 | 48 |
| methylthiomethyl octanoate | — | 2.5 | — |
| methylthiomethyl heptanoate | — | — | 2.5 |
| propylene glycol | 680 | 677.5 | 677.5 |
|  | 1000.0 | 1000.0 | 1000.0 |

Mixtures A, B and C were added separately to a test solution (containing 10% sugar and 0.05% citric acid) at a level of 0.1 g. per liter. The flavored solutions were tasted and compared. As compared with mixture A, the taste of mixture B is preferred because it is more pineapple-like with a more natural taste and aftertaste. As compared with mixture A, the taste of mixture C is preferred because it has a better pineapple character with increased fruitiness and the heavy natural sweetness of the genuine fruit.

EXAMPLE 20

Two strawberry flavor compositions were prepared by mixing the following ingredients:

|  | A | B |
|---|---|---|
| maltol | 30 | 30 |
| cis-3-hexenol | 0.6 | 0.6 |
| ethyl isovalerate | 1 | 1 |
| γ-undecalactone | 3 | 3 |
| benzyl butyrate | 3 | 3 |
| ethyl butyrate | 20 | 20 |
| ethyl acetate | 1 | 1 |
| amyl acetate | 1 | 1 |
| geranyl acetate | 0.1 | 0.1 |
| diacetyl | 0.1 | 0.1 |
| γ-nonalactone | 0.1 | 0.1 |
| β-terpineol | 0.08 | 0.08 |
| Ylang Ylang oil | 0.02 | 0.02 |
| Orange oil | 0.3 | 0.3 |
| phenylethyl isovalerate | 2.2 | 2.2 |
| methylthiomethyl isobutyrate | — | 2.5 |
| propylene glycol | 937.50 | 935.00 |
|  | 1000.00 | 1000.00 |

Mixtures A and B were added separately to a test solution (containing 10% sugar and 0.05% citric acid) at a level of 0.2 g. per liter. The flavored test solutions were compared. The test solution containing mixture B was preferred over the test solution containing mixture A because it has an improved strawberry character with notes reminiscent of a ripe, jammy strawberry. Similar notes were not found in the test solution containing mixture A.

EXAMPLE 21

Three cream flavor compositions were prepared by mixing the following ingredients:

|  | A | B | C |
|---|---|---|---|
| acetoin | 30 | 30 | 30 |
| diacetyl | 20 | 20 | 20 |
| vanillin | 20 | 20 | 20 |
| ethyl butyrate | 10 | 10 | 10 |
| maltol | 5 | 5 | 5 |
| δ-decalactone | 10 | 10 | 10 |
| ethyl lactate | 50 | 50 | 50 |
| butyric acid | 50 | 50 | 50 |
| hexanoic acid | 5 | 5 | 5 |

-continued

|  | A | B | C |
|---|---|---|---|
| methylthiomethyl propionate | — | 2.5 | — |
| methylthiomethyl butyrate | — | — | 0.5 |
| propylene glycol | 800 | 797.5 | 799.5 |
|  | 1000.0 | 1000.0 | 1000.0 |

Mixtures A, B and C were added separately to a test solution (containing 8% sugar) at a level of 0.2 g. per liter. The flavored solutions were tasted and compared. As compared with mixture A, the taste of mixture B is more pronounced cream-like, having an improved dairy character. The test solution containing mixture B was therefore preferred over the test solution containing mixture A. As compared to mixture A, the taste of mixture C is preferred because it showed a fuller, richer, more cream-like character, with enhanced sweet notes.

EXAMPLE 22

Two mango flavor compositions were prepared by mixing the following ingredients:

|  | A | B |
|---|---|---|
| ethylmaltol | 20 | 20 |
| vanillin | 4.5 | 4.5 |
| isopropyl alcohol | 300 | 300 |
| mandarin oil | 5 | 5 |
| ethyl acetate | 3 | 3 |
| orange essence oil | 4 | 4 |
| 2-methylbutyric acid | 3.5 | 3.5 |
| cis-3-hexenol | 5.5 | 5.5 |
| γ-undecalactone | 1 | 1 |
| propylene glycol | 653.5 | 646 |
| methylthiomethyl-2-methylbutyrate | — | 7.5 |
|  | 1000.0 | 1000.0 |

Mixtures A and B were added separately to a test solution (containing 10% sugar and 0.05% citric acid) at a level of 0.2 g. per liter. The flavored solutions were tasted and compared. As compared with mixture A, the taste of mixture B is more mango-like with a typical sulfury, fruity, tropical note which is important for this fruit. Since this note was not found in the test solution containing mixture A, the test solution containing mixture B was preferred.

EXAMPLE 23

Three blackcurrant flavor compositions were prepared by mixing the following ingredients:

|  | A | B | C |
|---|---|---|---|
| vanillin | 4 | 4 | 4 |
| angelicaroot oil | 6 | 6 | 6 |
| buchu oil | 100 | 100 | 100 |
| cognac oil (green) | 3 | 3 | 3 |
| mandarin oil | 4 | 4 | 4 |
| petitgrain oil | 10 | 10 | 10 |
| cedar leaf oil | 3 | 3 | 3 |
| isoamyl isovalerate | 15 | 15 | 15 |
| isoamyl butyrate | 4 | 4 | 4 |
| methyl butyrate | 20 | 20 | 20 |
| ethyl butyrate | 10 | 10 | 10 |
| ethyl hexanoate | 5 | 5 | 5 |
| isobutyl acetate | 120 | 120 | 120 |
| methyl isobutyl carbinylacetate | 20 | 20 | 20 |
| ethylbenzoate | 5 | 5 | 5 |
| bornyl acetate | 8 | 8 | 8 |
| citral | 2 | 2 | 2 |
| cuminic aldehyde | 3 | 3 | 3 |
| β-ionone | 3 | 3 | 3 |

-continued

|  | A | B | C |
|---|---|---|---|
| methylthiomethyl valerate | — | 10 | — |
| methylthiomethyl tiglate | — | — | 10 |
| propylene glycol | 655 | 645 | 645 |
|  | 1000.0 | 1000.0 | 1000.0 |

Mixtures A, B and C were added separately to a test solution (containing 10% sugar and 0.05% citric acid) at a level of 0.01 g. per liter. The flavored solutions were tasted and compared. As compared with mixture A, the taste of mixture B is preferred because it has a better blackcurrant flavor with a fresh, fruity topnote reminiscent of the fresh fruit. As compared with mixture A, the taste of mixture C is preferred because it has a blackcurrant flavor with increased sweet body notes giving a richer fuller fruity character.

EXAMPLE 24

Two peach flavor compositions were prepared by mixing the following ingredients:

|  | A | B |
|---|---|---|
| vanillin | 4.5 | 4.5 |
| ethylmaltol | 20 | 20 |
| tangerine oil | 5 | 5 |
| ethyl acetate | 3 | 3 |
| benzyl acetate | 3 | 3 |
| orange peel oil | 4 | 4 |
| bergamot oil | 1 | 1 |
| 2-methylbutyric acid | 3.5 | 3.5 |
| cis-3-hexenol | 5.5 | 5.5 |
| benzyl alcohol | 15 | 15 |
| methylthiomethyl isovalerate | — | 5 |
| propylene glycol | 935.5 | 930.5 |
|  | 1000.0 | 1000.0 |

Mixtures A and B were added separately to a test solution (containing 10% sugar and 0.05% citric acid) at a level of 0.2 g. per liter. The flavored solutions were tasted and compared. As compared with mixture A, the taste of mixture B is preferred because it has a better peach character with improved aftertaste and a sweet jammy note reminiscent of ripe peach.

EXAMPLE 25

Two condensed milk flavor compositions were prepared by mixing the following ingredients:

|  | A | B |
|---|---|---|
| heliotropin | 1 | 1 |
| vanillin | 20 | 20 |
| maltol | 5 | 5 |
| acetoin | 40 | 40 |
| diacetyl | 20 | 20 |
| ethyl butyrate | 8 | 8 |
| ethyl hexanoate | 2 | 2 |
| δ-decalactone | 10 | 10 |
| γ-nonalactone | 1 | 1 |
| n-butyric acid | 40 | 40 |
| hexanoic acid | 4 | 4 |
| methylthiomethyl 2-hexenoate | — | 5 |
| propylene glycol | 849 | 844 |
|  | 1000.0 | 1000.0 |

Mixtures A and B were added separately to a test solution (containing 8% sugar) at a level of 0.2 g. per liter. The flavored solutions were tasted and compared. As compared with mixture A, the taste of mixture B is preferred because it has a pronounced cooked milk character with a richer creamier aftertaste.

EXAMPLE 26

Two grape flavor compositions were prepared by mixing the following ingredients:

|  | A | B |
|---|---|---|
| maltol | 0.25 | 0.25 |
| cognac oil (green) | 0.1 | 0.1 |
| lime oil | 0.4 | 0.4 |
| orange oil terpenes | 0.8 | 0.8 |
| isoamyl acetate | 0.3 | 0.3 |
| fusel oil | 2 | 2 |
| ethyl acetate | 2 | 2 |
| ethyl butyrate | 0.4 | 0.4 |
| lie de vin | 0.1 | 0.1 |
| ethyl 2-methylbutyrate | 0.3 | 0.3 |
| 2-methylbutanol | 2 | 2 |
| citral | 0.05 | 0.05 |
| phenylethyl alcohol | 0.25 | 0.25 |
| trans-2-hexenol | 0.1 | 0.1 |
| methyl anthranilate | 10 | 6 |
| methylthiomethyl lavandulate | — | 4 |
| propylene glycol | 980.95 | 980.95 |
|  | 1000.0 | 1000.0 |

Mixtures A and B were added separately to a test solution (containing 10% sugar and 0.05% citric acid) at a level of 0.2 g. per liter. The flavored solutions were tasted and compared. As compared with mixture A, the taste of mixture B is preferred because it has an improved grape character with a more natural aftertaste and does not have the harsh methyl anthranilate taste shown by mixture A.

What we claim and desire to protect by Letters Patent is:

1. A fruit or berry flavoring composition or a fruit or berry flavor-enhancing composition comprising a combination of olfactorily active ingredients including at least one methylthiomethyl ester having the structural formula R—COOCH$_2$—S—CH$_3$ wherein R is selected from the class consisting of hydrogen, alkyl radicals with 2 to 9 carbon atoms, alkenyl radicals with 2 to 9 carbon atoms, and polyunsaturated radicals with 4 to 9 carbon atoms and at least one compound selected from the class consisting of:
   orange oil
   isoamyl acetate
   phenyl ethyl isovalerate
   fusel oil
   damascenone
   lie de vin
   ethyl maltol
   2-methyl butanol
   2-methylbutyric acid
   phenylethyl alcohol
   angelica root oil
   trans-2-hexenol
   buchu oil
   methyl anthranilate
   cognac oil
   2-methyl-2-pentenoic acid
   petitgrain oil
   vanillin
   cedar leaf oil
   maltol
   isoamyl isovalerate
   benzyl alcohol
   methyl butyrate linaolool
isobutyl acetate
isoamyl butyrate
methyl isobutyl carbinyl acetate
ethyl acetate
ethyl butyrate
ethyl benzoate
ethyl hexanoate
citral
ethyl heptanoate
cuminic aldehyde
cis-3-hexenol
beta-ionone
ethyl isovalerate
tangerine oil
phenyl butyrate
benzyl acetate
amyl acetate
orange peel oil
geranyl acetate
bergamot oil
gamma-nonalactone
lime oil
Ylang Ylang
orange terpenes
beta-terpineol
methyl cinnamate.

2. A flavoring composition according to claim 1 wherein R is hydrogen or an alkyl radical with 1 to 9 carbon atoms.

3. The flavoring composition according to claim 2 wherein the ester is methylthiomethyl butyrate.

4. The flavoring composition according to claim 2 wherein the ester is methylthiomethyl isobutyrate.

5. The flavoring composition according to claim 2 wherein the ester is methylthiomethyl 2-methylbutyrate.

6. The flavoring composition according to claim 2 wherein the ester is methylthiomethyl valerate.

7. The flavoring composition according to claim 2 wherein the ester is methylthiomethyl isovalerate.

8. The flavoring composition according to claim 2 wherein the ester is methylthiomethyl hexanoate.

9. The flavoring composition according to claim 2 wherein the ester is methylthiomethyl heptanoate.

10. The flavoring composition according to claim 2 wherein the ester is methylthiomethyl octanoate.

11. A flavoring composition according to claim 1 wherein R is an alkenyl radical with 2 to 9 carbon atoms.

12. The flavoring composition according to claim 11 wherein the ester is methylthiomethyl tiglate.

13. The flavoring composition according to claim 11 wherein the ester is methylthiomethyl 2-hexenoate.

14. The flavoring composition according to claim 11 wherein the ester is methylthiomethyl 2-methyl-2-pentenoate.

15. A flavoring composition according to claim 1 wherein R is a polyunsaturated alkyl radical with 4 to 9 carbon atoms.

16. The flavoring composition according to claim 15 wherein the ester is methylthiomethyl lavandulate.

17. A foodstuff to which has been added about 0.1 to 5 parts per million, based on the total weight of said foodstuff, of at least one methylthiomethyl ester having the structural formula R—COOCH$_2$SCH$_3$ wherein R is selected from the class consisting of hydrogen, alkyl radicals with 1 to 9 carbon atoms, alkenyl radicals with 2 to 9 carbon atoms and polyunsaturated alkyl radicals with 4 to 9 carbon atoms.

18. A foodstuff according to claim 17 wherein R is hydrogen or an alkyl radical with 1 to 9 carbon atoms.

19. The foodstuff of claim 18 wherein the ester is methylthiomethyl butyrate.

20. The foodstuff of claim 18 wherein the ester is methylthiomethyl isobutyrate.

21. The foodstuff of claim 18 wherein the ester is methylthiomethyl 2-methylbutyrate.

22. The foodstuff of claim 18 wherein the ester is methylthiomethyl valerate.

23. The foodstuff of claim 18 wherein the ester is methylthiomethyl isovalerate.

24. The foodstuff of claim 18 wherein the ester is methylthiomethyl hexanoate.

25. The foodstuff of claim 18 wherein the ester is methylthiomethyl heptanoate.

26. The foodstuff of claim 18 wherein the ester is methylthiomethyl octanoate.

27. A foodstuff according to claim 17 wherein R is an alkenyl radical with 2 to 9 carbon atoms.

28. The foodstuff of claim 27 wherein the ester is methylthiomethyl tiglate.

29. The foodstuff of claim 27 wherein the ester is methylthiomethyl 2-hexenoate.

30. The foodstuff of claim 27 wherein the ester is methylthiomethyl 2-methyl-2-pentenoate.

31. A foodstuff according to claim 17 wherein R is a polyunsaturated alkyl radical with 4 to 9 carbon atoms.

32. The foodstuff of claim 31 wherein the ester is methylthiomethyl lavandulate.

33. A method of improving the flavor of a foodstuff which comprises adding thereto about 0.1 to 5 parts per million of at least one methylthiomethyl ester having the structural formula R—COOCH$_2$SCH$_3$ wherein R is selected from the class consisting of hydrogen, alkyl radicals with 1 to 9 carbon atoms, alkenyl radicals with 2 to 9 carbon atoms and polyunsaturated alkyl radicals with 4 to 9 carbon atoms.

* * * * *